US010856895B2

(12) United States Patent
Fukui et al.

(10) Patent No.: US 10,856,895 B2
(45) Date of Patent: Dec. 8, 2020

(54) OBJECT SUCTION DEVICE

(71) Applicant: NIPPON FRONTIER MEDICINE LABORATORIES, INC., Osaka (JP)

(72) Inventors: Junichi Fukui, Osaka (JP); Kunihiro Musashi, Osaka (JP)

(73) Assignee: NIPPON FRONTIER MEDICINE LABORATORIES, INC., Osaka (JP)

( * ) Notice: Subject to any disclaimer, the term of this patent is extended or adjusted under 35 U.S.C. 154(b) by 206 days.

(21) Appl. No.: 16/062,494

(22) PCT Filed: Dec. 16, 2016

(86) PCT No.: PCT/JP2016/087686
§ 371 (c)(1),
(2) Date: Jun. 14, 2018

(87) PCT Pub. No.: WO2017/104846
PCT Pub. Date: Jun. 22, 2017

(65) Prior Publication Data
US 2018/0368872 A1    Dec. 27, 2018

(30) Foreign Application Priority Data

Dec. 16, 2015   (JP) ................................. 2015-244730

(51) Int. Cl.
*A61B 17/32*       (2006.01)
*A61B 17/3205*     (2006.01)
*A61B 17/3207*     (2006.01)

(52) U.S. Cl.
CPC .... *A61B 17/32002* (2013.01); *A61B 17/3205* (2013.01); *A61B 17/320758* (2013.01); *A61B 17/320783* (2013.01); *A61B 2217/005* (2013.01)

(58) Field of Classification Search
CPC ............ A61B 17/32002–2017/320032; A61B 17/320758–2017/320791;
(Continued)

(56) References Cited

U.S. PATENT DOCUMENTS 5,314,407 A    5/1994 Auth et al.
5,383,884 A    1/1995 Summers
(Continued)

FOREIGN PATENT DOCUMENTS

CN    201091599    7/2008
CN    102348418    2/2012
(Continued)

OTHER PUBLICATIONS

European search report dated Jun. 26, 2019 in European Patent Application No. 16875820.9.
(Continued)

*Primary Examiner* — Tan-Uyen T Ho
*Assistant Examiner* — Charles M Wei
(74) *Attorney, Agent, or Firm* — Ladas & Parry LLP (57) ABSTRACT

An object suction device that more effectively sucks an object includes a pipe, a rotating member that is rotatably provided in the pipe and conveys an object that enters from an opening portion provided at a distal end of the pipe toward a rear end of the pipe, an air motor that rotates the rotating member, a nozzle that sucks the object discharged from the rear end of the pipe, and a channel that is connected to both the nozzle and the air motor and forms a flow of air and the object.

3 Claims, 11 Drawing Sheets

(58) Field of Classification Search
CPC .... A61B 2010/0208–045; B25B 19/44; A47L 5/00–11/00
See application file for complete search history.

(56) References Cited

U.S. PATENT DOCUMENTS

| | | | |
|---|---|---|---|
| 5,569,275 | A | 10/1996 | Kotula et al. |
| 5,695,513 | A | 12/1997 | Johnson et al. |
| 6,997,867 | B2* | 2/2006 | Soble ............... A61B 1/005 600/121 |
| 8,070,765 | B2 | 12/2011 | Oliver et al. |
| 2002/0082519 | A1* | 6/2002 | Miller ............... A61B 10/025 600/566 |
| 2003/0114875 | A1 | 6/2003 | Sjostrom |
| 2007/0198042 | A1* | 8/2007 | Richard ............ A61B 17/3472 606/185 |
| 2008/0208229 | A1 | 8/2008 | Tidwell et al. |
| 2010/0152615 | A1* | 6/2010 | Mark ............... A61B 10/0275 600/567 |
| 2012/0004595 | A1* | 1/2012 | Dubois ............ A61B 17/32002 604/22 |
| 2012/0172905 | A1* | 7/2012 | Lee Shee ........ A61B 17/32002 606/180 |
| 2012/0283742 | A1 | 11/2012 | Dubois et al. |
| 2013/0046199 | A1 | 2/2013 | Dubois et al. |
| 2013/0211438 | A1 | 8/2013 | Dubois et al. |
| 2013/0218186 | A1* | 8/2013 | Dubois ............ A61B 17/32002 606/180 |
| 2013/0310834 | A1 | 11/2013 | Dubois et al. |
| 2014/0081266 | A1 | 3/2014 | Dubois et al. |
| 2014/0140815 | A1 | 5/2014 | Shener-Irmakoglu et al. |
| 2015/0150580 | A1 | 6/2015 | Dubois et al. |
| 2015/0201995 | A1* | 7/2015 | Dubois ............ A61B 17/32002 606/41 |

FOREIGN PATENT DOCUMENTS

| | | |
|---|---|---|
| CN | 103068327 | 4/2013 |
| CN | 103281974 | 9/2013 |
| JP | S60132711 U | 9/1985 |
| JP | 63212339 A | 9/1988 |
| JP | 03133449 A | 6/1991 |
| JP | 09508554 A | 9/1997 |
| JP | 2000505665 A | 5/2000 |
| JP | 2010519961 A | 6/2010 |
| JP | 20100240467 A | 10/2010 |
| JP | 2015171633 A | 10/2015 |
| JP | 5813193 B1 | 11/2015 |
| JP | 2015534889 A | 12/2015 |
| WO | 02076283 A2 | 10/2002 |
| WO | 2013/111936 A1 | 8/2013 |
| WO | 2014028046 | 2/2014 |

OTHER PUBLICATIONS

Japanese Office Action dated Jun. 11, 2019 in Japanese Patent Application No. 2017-556489 and its English translation.
Japanese Office Action dated Sep. 13, 2018 of Japanese Patent Application No. 2017-556489 and its English translation.
International Search Report for PCT/JP2016/087686 dated Mar. 7, 2016, 8 pp.
Chinese Office Action dated Jun. 19, 2020 in Chinese Patent Application No. 201680071568.X and its English translation.

* cited by examiner

OBJECT SUCTION DEVICE

CROSS-REFERENCE TO RELATED APPLICATIONS

This application is a U.S. National Stage filing under 35 U.S.C. § 371 and 35 U.S.C. § 119 based on and claiming the benefit of PCT/JP2016/087686, filed on Dec. 12, 2016, and claiming the benefit of Japanese Patent Application No. 2015-244730, filed on Dec. 16, 2015, both of which are hereby incorporated by reference herein in their entireties.

TECHNICAL FIELD

The present invention relates to an object suction device that sucks an object.

BACKGROUND

As a tool used to remove an object, for example, devices disclosed in patent references 1 to 3 are known.
Patent reference 1: U.S. Pat. No. 5,383,884
Patent reference 2: WO 02/076283
Patent reference 3: Japanese Patent Laid-Open No. 2010-240467

SUMMARY OF THE INVENTION

In patent references 1 to 3, since a cutter is rotated using an electric motor, the vibration of the electric motor is transmitted to the cutter, resulting in difficulty in removing a tissue.

The present invention enables to solve the above-described problem.

One example aspect of the present invention provides an object suction device comprising:
a pipe;
a rotating member that is rotatably provided in the pipe and conveys an object that enters from an opening portion provided at a distal end of the pipe toward a rear end of the pipe;
an air motor that rotates the rotating member;
a nozzle that sucks the object discharged from the rear end of the pipe;
and
a channel that is connected to both the nozzle and the air motor and forms a flow of air and the object.

According to the present invention, it is possible to more effectively remove an object.

DESCRIPTION OF EXAMPLE EMBODIMENTS

Example embodiments of the present invention will now be described in detail with reference to the drawings. It should be noted that the relative arrangement of the components, the numerical expressions and numerical values set forth in these example embodiments do not limit the scope of the present invention unless it is specifically stated otherwise.

First Example Embodiment

Figure 1:
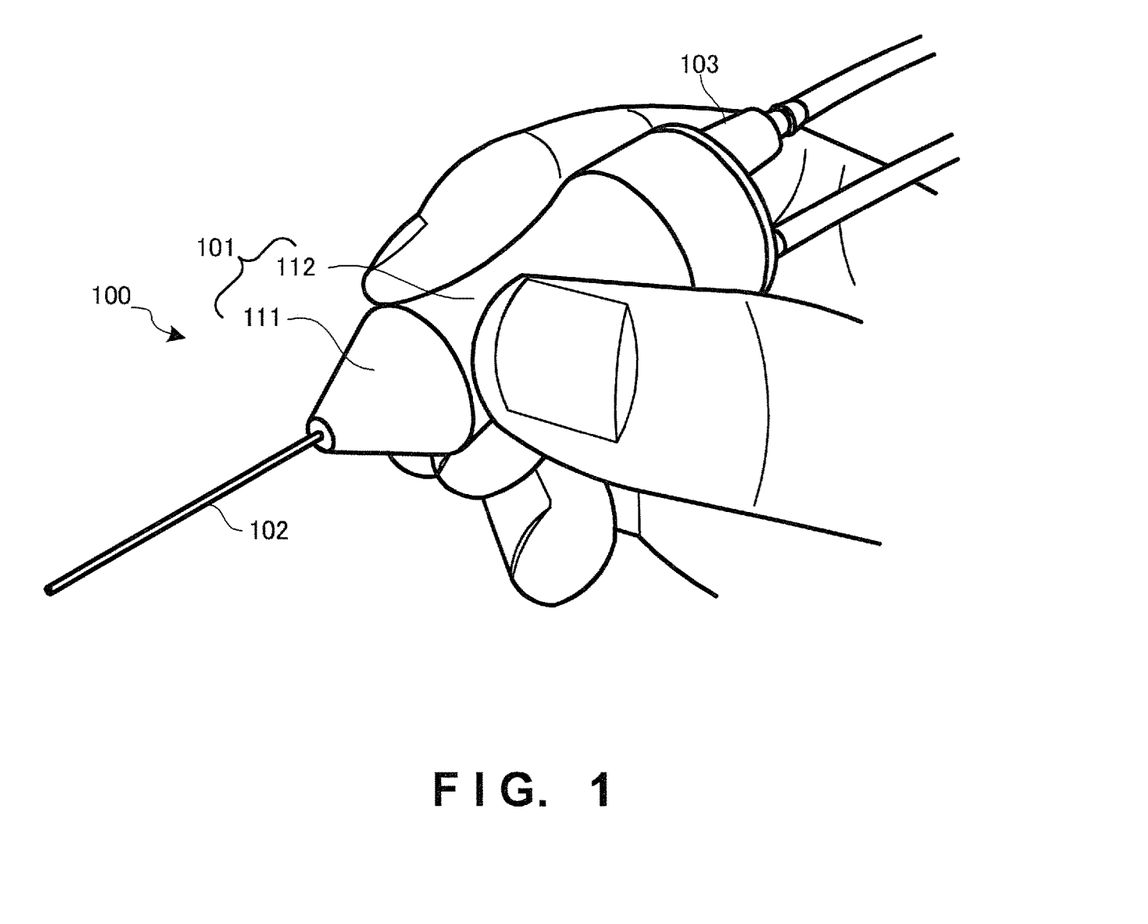
FIG. 1 is a perspective view of an object suction device according to the first example embodiment of the present invention.

FIG. 1 is a perspective view of an object suction device according to the first example embodiment of the present invention. As shown in FIG. 1, an object suction device 100 includes a body 101 including a conical portion 111 and a grip 112, a pipe 102 extending from the small-diameter-side distal end of the conical portion 111, and a connecting portion 103 provided at an end of the body 101 on the opposite side of the conical portion 111. A vacuum suction source (not shown) such as a vacuum pump is connected to the connecting portion 103. As for the usage, for example, an operator can hold the grip 112 by fingertips, insert the pipe 102 into a living body, cut a biotissue at the distal end of the pipe 102, suck the biotissue, and discharge it out of the body.

Figure 2:
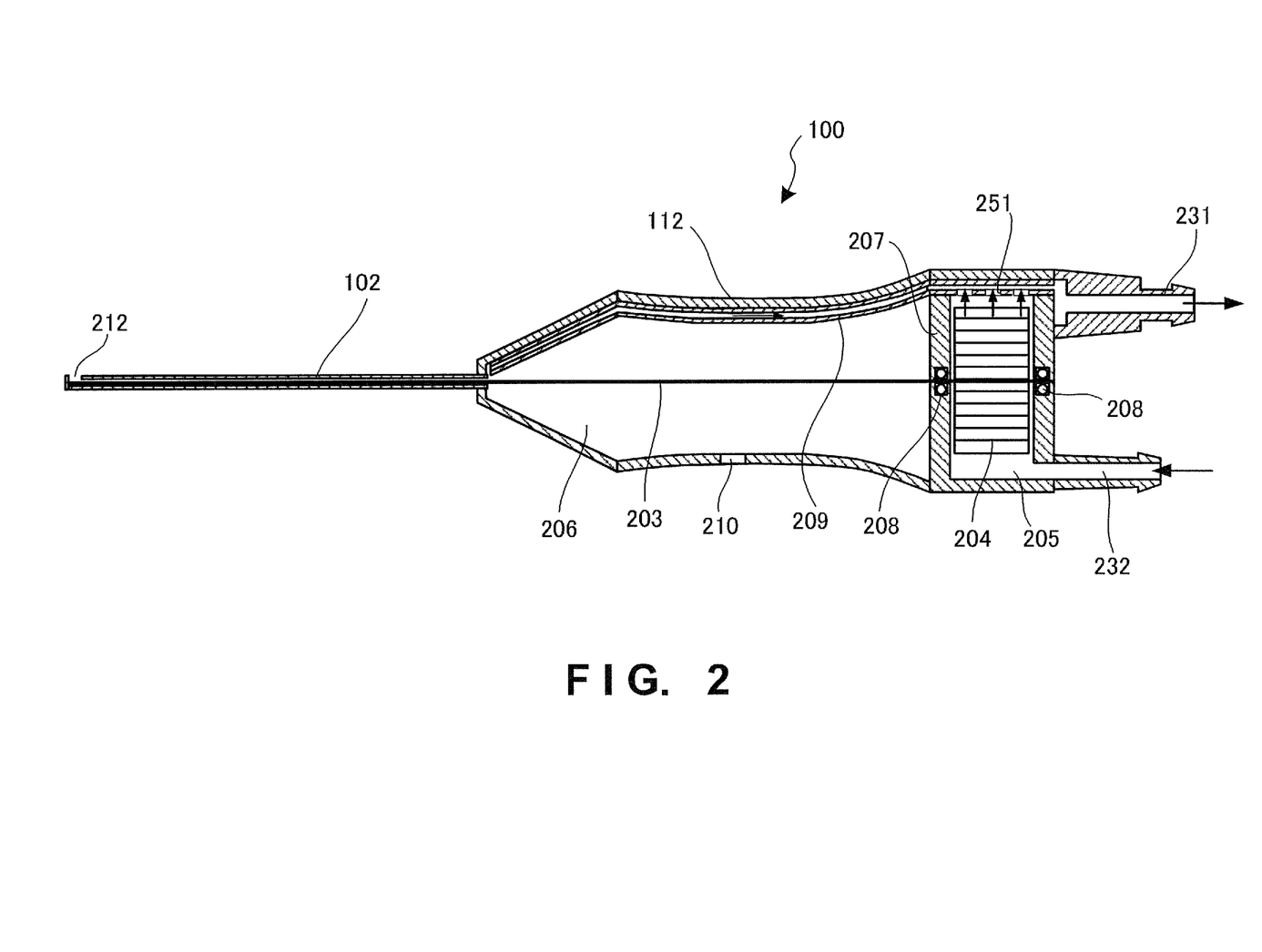
FIG. 2 is a sectional view of the object suction device according to the first example embodiment of the present invention.

FIG. 2 is a sectional view of the object suction device 100. An opening portion 212 is formed at the distal end of the pipe 102. The distal end of a rotating member 203 is rotatably inserted into the pipe 102.

The body 101 includes a storage chamber 206 configured to store an object conveyed by the rotating member 203 from the opening portion 212 at the distal end of the pipe 102, and a rotation chamber 205 arranged on the rear end side of the storage chamber 206. The storage chamber 206 and the rotation chamber 205 are isolated by a partition 207.

The rear end of the rotating member 203 extends up to the rotation chamber 205 via the storage chamber 206 and is rotatably supported by a bearing 208. An air motor 204 is arranged in the rotation chamber 205, and the rotating member 203 is fixed to the rotating shaft of the air motor 204. For this reason, as the air motor 204 rotates, the rotating member 203 rotates.

At least one opening 251 is provided in a side wall of the rotation chamber 205, which is located on the outer side viewed from the rotating shaft of the air motor 204 and is close to a nozzle 231. The rotation chamber 205 communicates with a channel 209 via the opening 251. A side wall of the rotation chamber 205, which is located on the outer side viewed from the rotating shaft of the air motor 204 and located on the opposite side of the opening 251, communicates with a nozzle 232.

The nozzle 231 is connected to one end side of the tubular channel 209 arranged inside the body 101. The other end of the channel 209 extends to the vicinity of the rear end side of the pipe 102 facing the storage chamber 206.

When the nozzle 231 is connected to a suction pump (not shown) and vacuum-sucked, air that enters from the nozzle 232 rotates the air motor 204 and the rotating member 203.

The material of the pipe 102 and the rotating member 203 is not particularly limited. However, a high-rigidity material that hardly causes deflection is preferably used. Examples are a fine ceramic such as zirconia, a hard metal such as tungsten carbide, and a metal material such as stainless steel.

Figure 3:
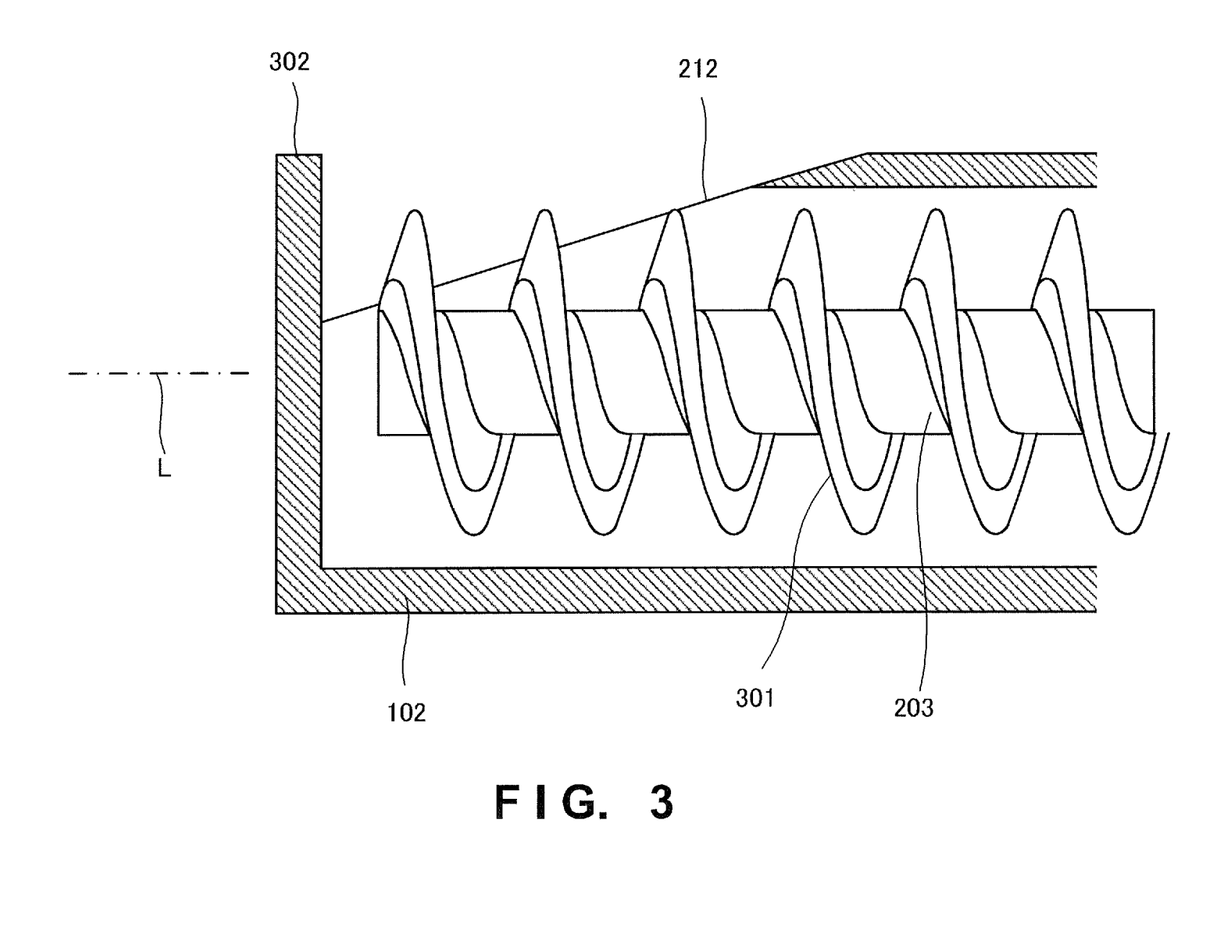
FIG. 3 is a partially enlarged sectional view of the object suction device according to the first example embodiment of the present invention.
Figure 4:
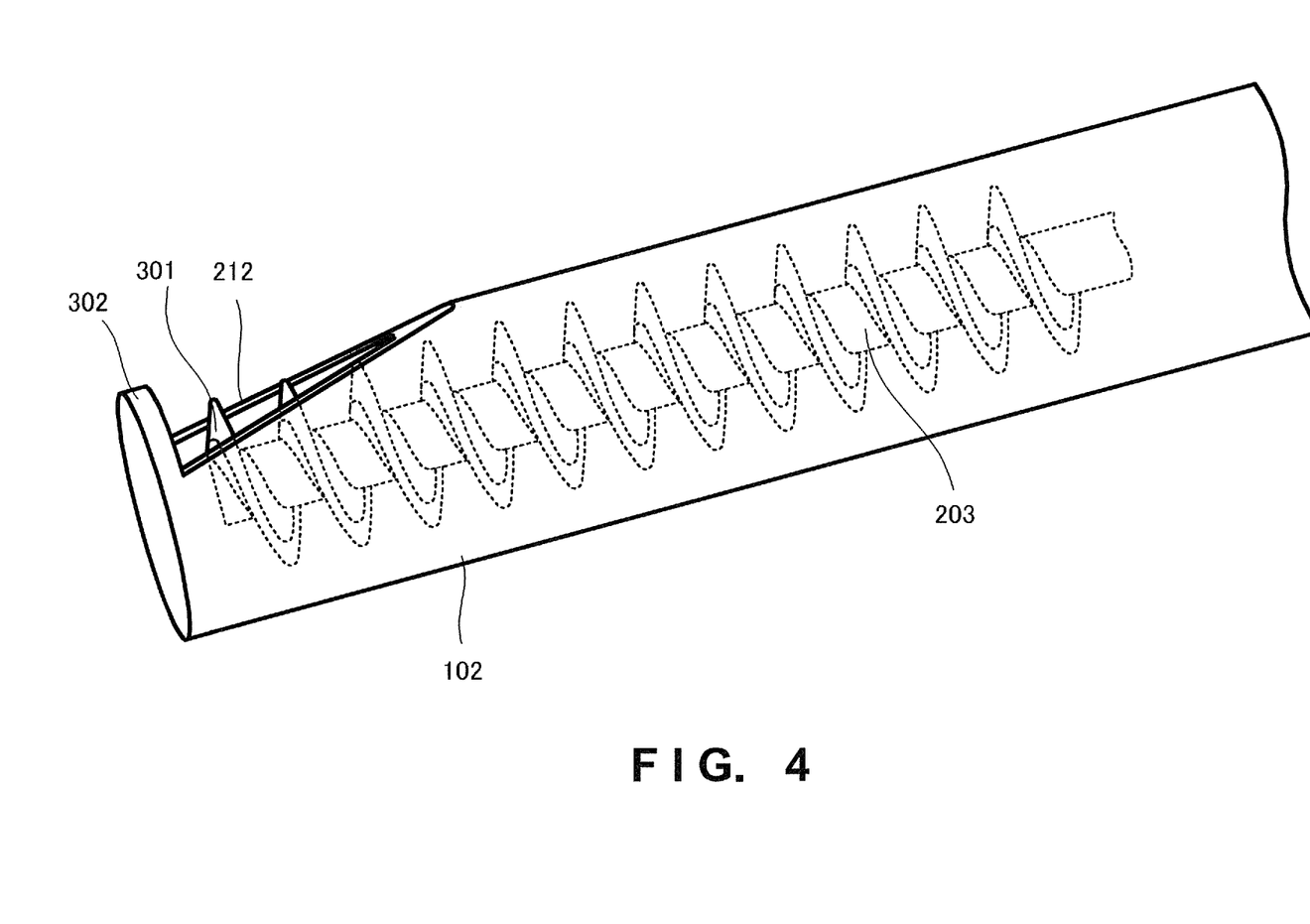
FIG. 4 is a partial perspective view of the object suction device according to the first example embodiment of the present invention.

FIG. 3 is a sectional view showing the distal end of the pipe 102 in an enlarged state. FIG. 4 is a perspective view of the distal end of the pipe 102. The opening plane of the opening portion 212 tilts with respect to an axis L of the pipe 102 and the rotating member 203. A tip wall 302 is formed at the distal end of the pipe 102.

A spiral portion 301 is provided on the outer peripheral surface of the rotating member 203 on the distal end side. When the rotating member 203 rotates, an object that enters from the opening portion 212 into the pipe 102 is conveyed to the rear end side of the pipe 102. The spiral portion 301 provided on the distal end side of the rotating member 203 is exposed from the opening portion 212, and can cut an object along with the rotation of the rotating member 203. In addition, the spiral portion 301 can also cut an object introduced from the opening portion 212 into the pipe 102.

Figure 5:
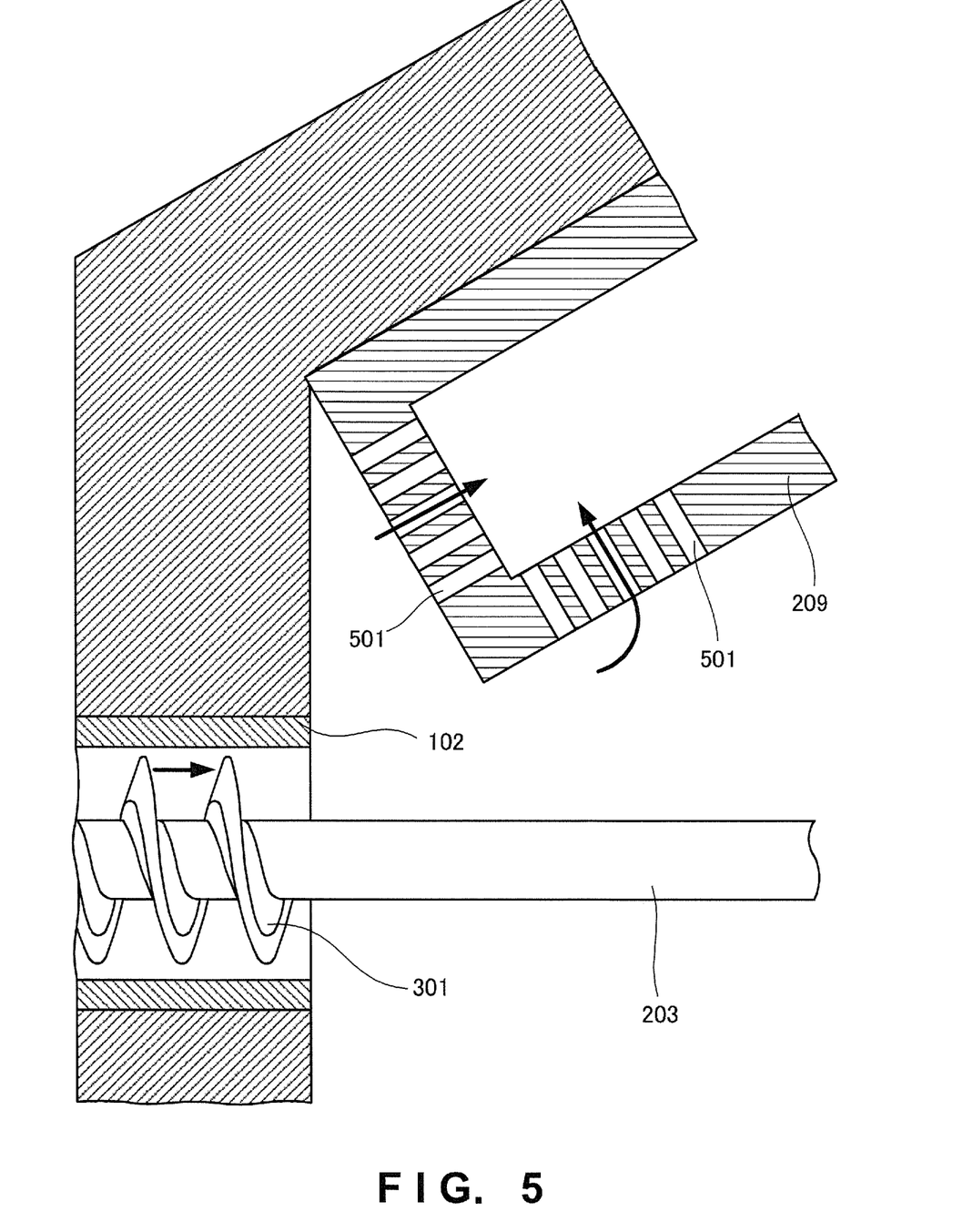
FIG. 5 is a partially enlarged sectional view of the object suction device according to the first example embodiment of the present invention.

FIG. 5 is a sectional view showing the rear end of the pipe 102 in an enlarged state. At least one vent hole 501 is formed at the distal end of the channel 209. When vacuum suction is performed via the nozzle 231, a negative pressure is formed in the storage chamber 206, and an object is sucked from the opening portion of the pipe 102. The vent hole 501 preferably has such a size that passes a gas but cannot pass the object conveyed to the storage chamber 206 and, for example, an air permeable membrane or the like can also be used. Note that an auxiliary introducing portion 210 that communicates with the outside may be formed in the grip 112 of the body 101. In this case, when performing an operation, the device is used while closing the auxiliary introducing portion 210 by a finger or the like.

In the object suction device 100 having the above-described arrangement, when the vacuum source connected to the nozzle 231 is actuated, a suction force acts on the opening portion 212 of the pipe 102, and the rotating member 203 rotates. Hence, when the distal end of the pipe 102 is pressed against an object (for example, a jelly-like biotissue), the object is drawn from the opening portion 212 into the pipe 102. The rotating member 203 rotates in this state, thereby cutting the object.

The cut object is conveyed by the rotating member 203 to the rear end side (hand side) and stored in the storage chamber 206. Since the spiral portion 301 is formed on the surface of the rotating member 203 according to this example embodiment, and the object can be cut in the gap between the spiral portion 301 and the inner surface of the pipe 102 even during the conveyance of the object inside the pipe 102, the object can be fragmented and reliably conveyed. However, the spiral portion 301 can also be formed only on a portion where the rotating member 203 is exposed from the opening portion 212.

The spiral portion 301 according to this example embodiment has a predetermined pitch. However, to facilitate cutting of an object in the opening portion 212, the pitch may be narrowed on the distal end side. In addition, to facilitate conveyance of an object in the pipe 102, the pitch may be widened on the rear end side of the rotating member. To reliably prevent clogging of the pipe 102 by an object, the shaft of the rotating member 203 may be absent, and an arrangement in which a shaft body is connected to the rear end of the rotating member 203 may be employed. Note that an arrangement in which the spiral portion 301 does not project from the opening plane of the opening portion 212 may also be employed.

In the object suction device 100 according to this example embodiment, the body 101 includes the storage chamber 206 that stores an object conveyed in the pipe 102 by the rotating member, and the rotation chamber 205 in which the air motor 204 connected to the rotating member 203 is arranged. The storage chamber 206 and the rotation chamber 205 communicate with the outside via the nozzle 231. For this reason, when the storage chamber 206 and the rotation chamber 205 are vacuum-sucked from the nozzle 231, it is possible to rotate the rotating member 203 and suck an object from the opening portion 212.

Hence, since the electric motor that rotates and drives the rotating member 203 is unnecessary, the vibration of the electric motor is not transmitted to the distal end of the rotating member, unlike the conventional arrangement, and removal of an object can be performed easily and correctly.

Additionally, according to the above arrangement of this example embodiment, when the amount of an object conveyed in the pipe 102 increases, and the suction force from the opening portion 212 lowers, the flow rate of airflow in the rotation chamber 205 rises, and the rotation speed of the air motor 204 increases. Hence, the conveyance capability of the rotating member 203 can be increased. It is therefore possible to reliably convey a cut object.

Figure 6:
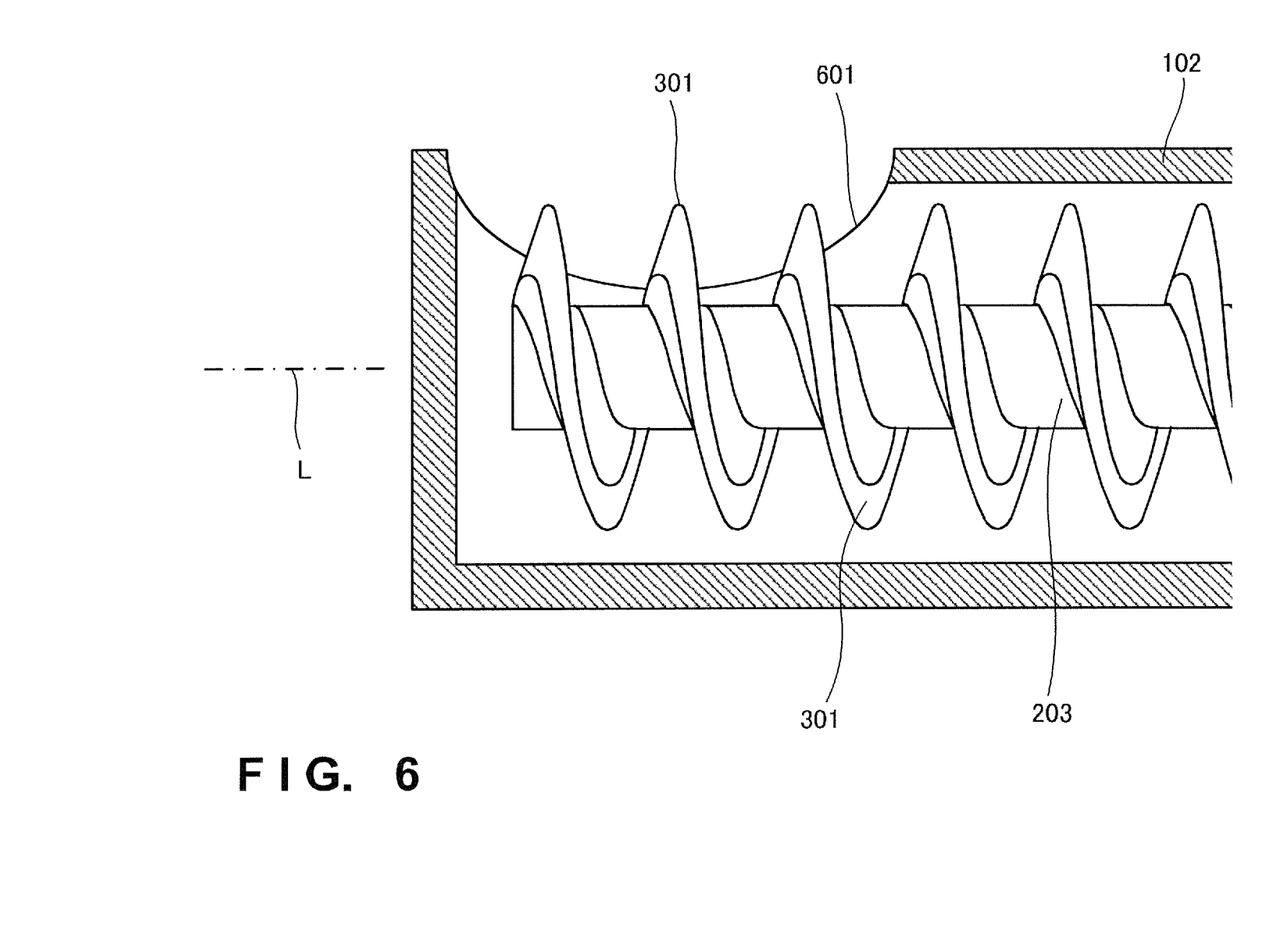
FIG. 6 is a partially enlarged sectional view of an object suction device according to a modification of the first example embodiment of the present invention.

Note that the shape of the pipe 102 is not limited to the shape shown in FIGS. 3 and 4. An arc opening 601 as shown in FIG. 6 may be formed.

The object suction device can be used when extracting a piece of a calculus such as a ureteral calculus or renal pelvic calculus crushed by an ultrasonic wave from a body.

Note that the device according to the above-described first example embodiment can also be expressed in the following way.

There is provided an object suction device including:

a hollow outer tube; a main body fixed to the base end of the outer tube; and a spiral conveyance member rotatably provided in the outer tube, the outer tube including an opening portion formed in an outer peripheral surface of a distal end, and the conveyance member including an edge portion that is formed along an outer edge and is exposed from the opening portion to cut a tissue and conveying the tissue received in the outer tube, wherein the main body includes a storage chamber that stores the tissue conveyed in the outer tube by the conveyance member, and a rotation chamber in which an impeller connected to the conveyance member is arranged, and the storage chamber and the rotation chamber communicate with an outside via a suction portion, and the storage chamber and the rotation chamber are vacuum-sucked from the suction portion, thereby rotating the conveyance member and sucking the tissue from the opening portion.

The rotation chamber is arranged on a base end side of the storage chamber, and the conveyance member is connected to the impeller via a shaft body.

Second Example Embodiment

An object suction device 700 according to the second example embodiment of the present invention will be described with reference to FIGS. 7 to 9. The object suction device 700 according to this example embodiment is different from the first example embodiment in the shape of a rotating member 703, the structure of the connecting portion between a pipe 102 and a channel 209, and the shape of an air motor 704. The rest of the components and operations is the same as in the first example embodiment. Hence, the same reference numerals denote the same components and operations, and a detailed description thereof will be omitted.

Figure 7:
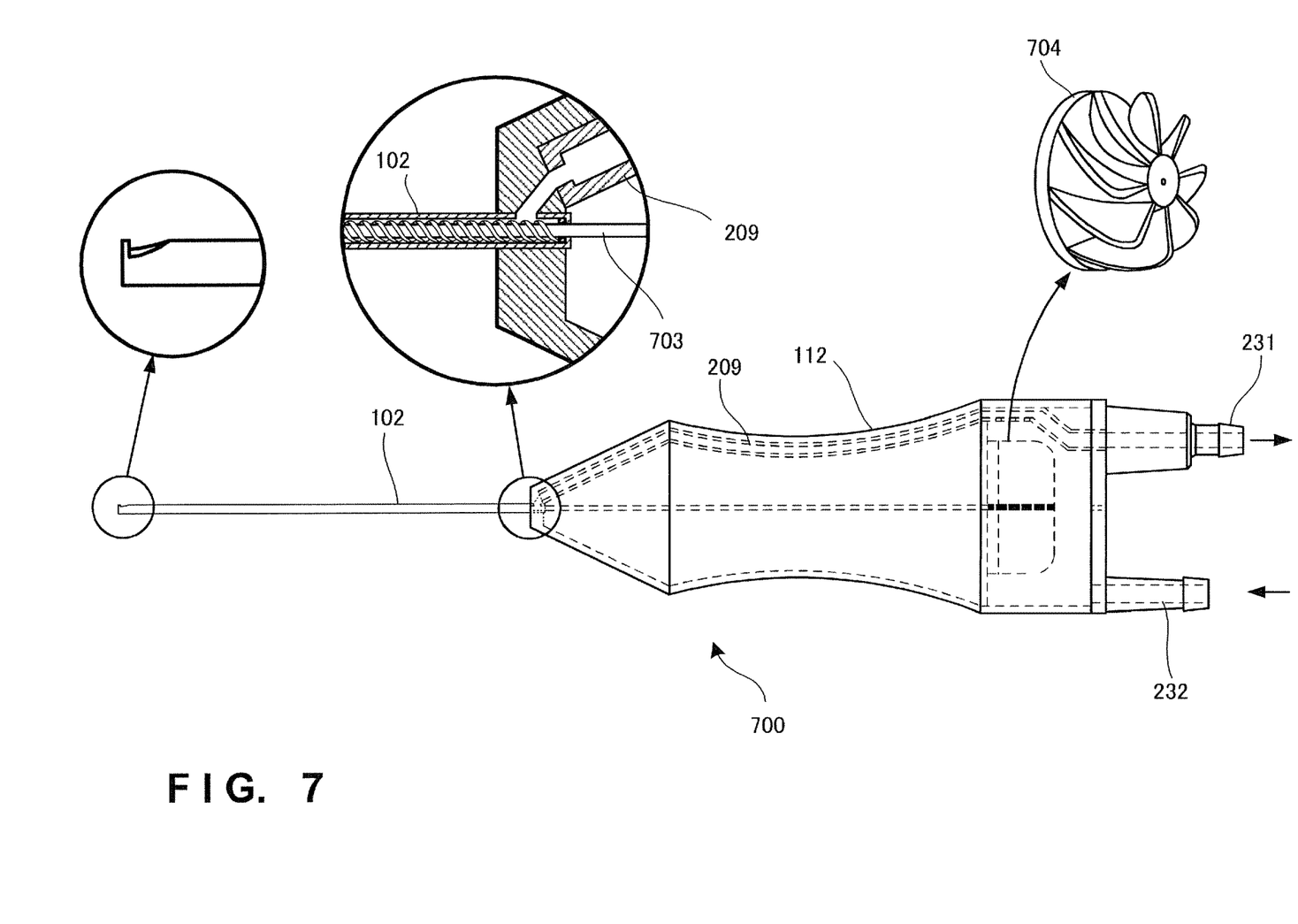
FIG. 7 is a schematic explanatory view of an object suction device according to the second example embodiment of the present invention.

FIG. 7 is a schematic explanatory view of the object suction device according to the second example embodiment of the present invention. FIG. 8 is a perspective view of the distal end portion of the pipe 102. FIG. 9 is a perspective view showing the arrangement of the rotating member 703.

Figure 8:
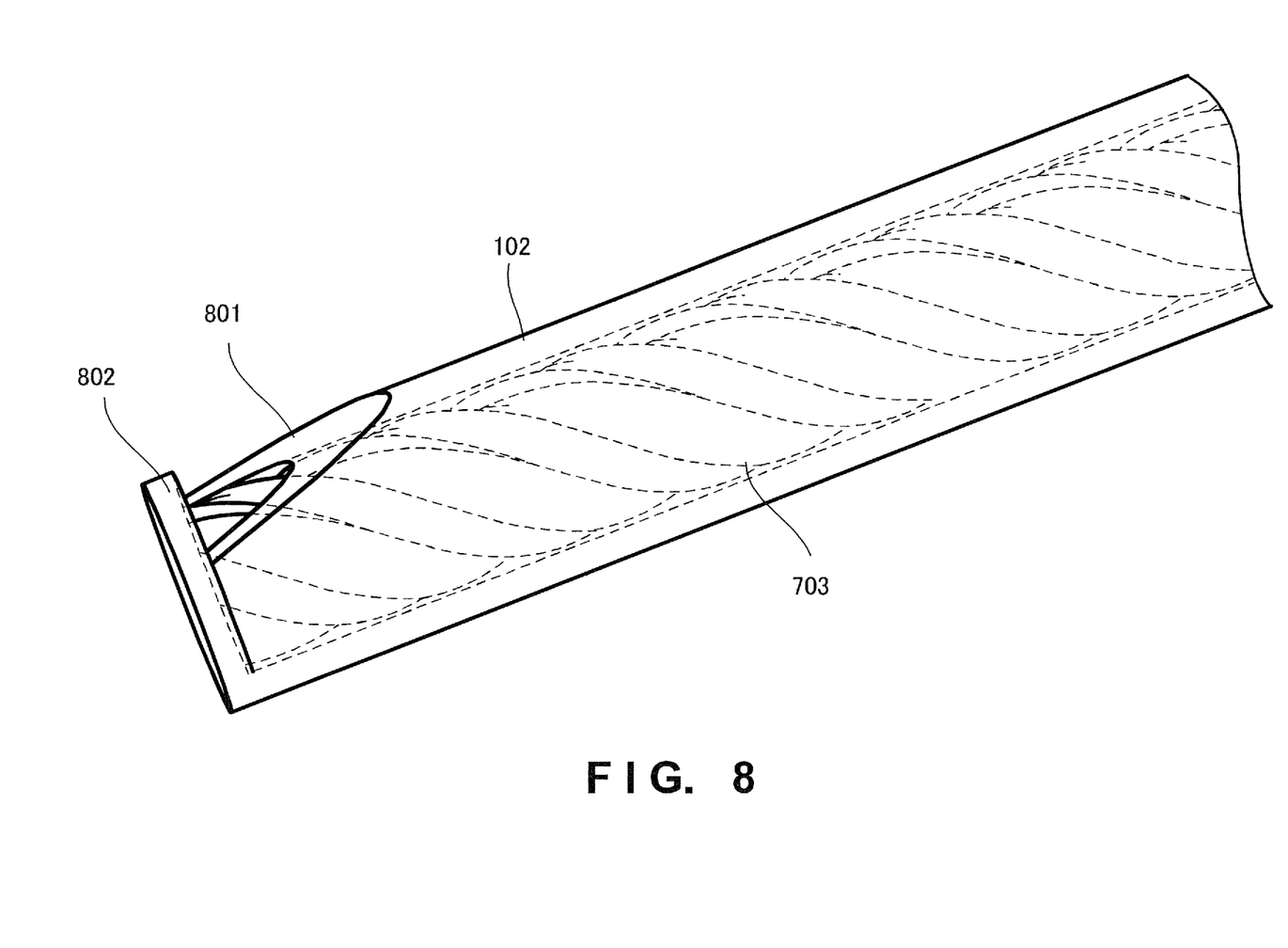
FIG. 8 is a partially enlarged perspective view of the object suction device according to the second example embodiment of the present invention.
Figure 9:
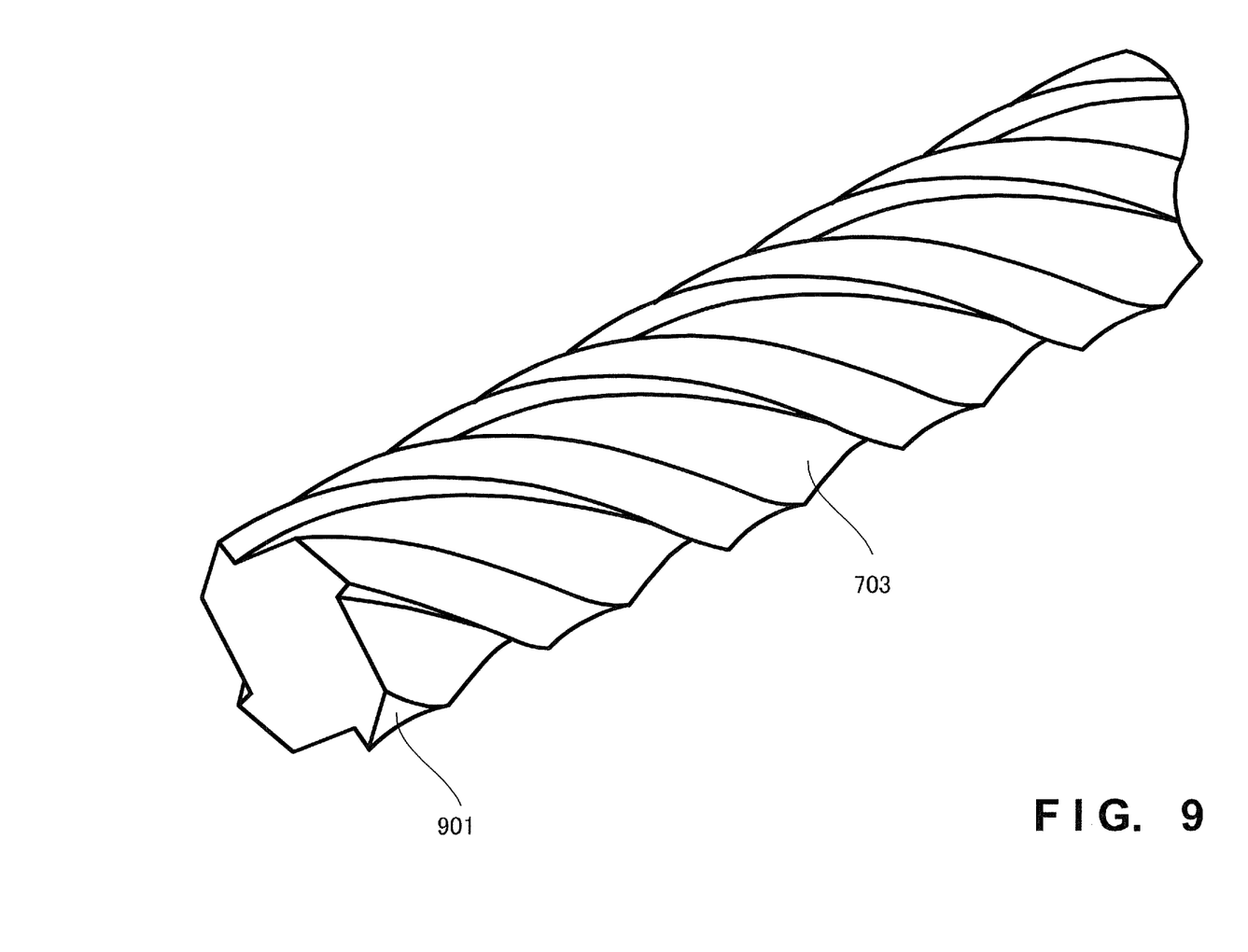
FIG. 9 is an enlarged perspective view of the rotating member of the object suction device according to the second example embodiment of the present invention.

As shown in FIGS. 8 and 9, the rotating member 703 has a drill shape, and the edge of a spiral portion 901 is formed as a sharp cutter. This allows the object suction device 700 to suck even a hard object such as a bone while crushing it. In this case, an opening 801 may be formed wider. In addition, an arrangement in which a tip wall 802 does not exist, and a part of the distal end of the rotating member 703 is uncovered may be employed.

Third Example Embodiment

An object suction device according to the third example embodiment of the present invention will be described with reference to FIG. 10. An object suction device 1000 according to this example embodiment is different from the second example embodiment in that a valve 1001 is provided in an opening portion 251 of a channel 209. The rest of the components and operations is the same as in the first example embodiment. Hence, the same reference numerals denote the same components and operations, and a detailed description thereof will be omitted.

Figure 10:
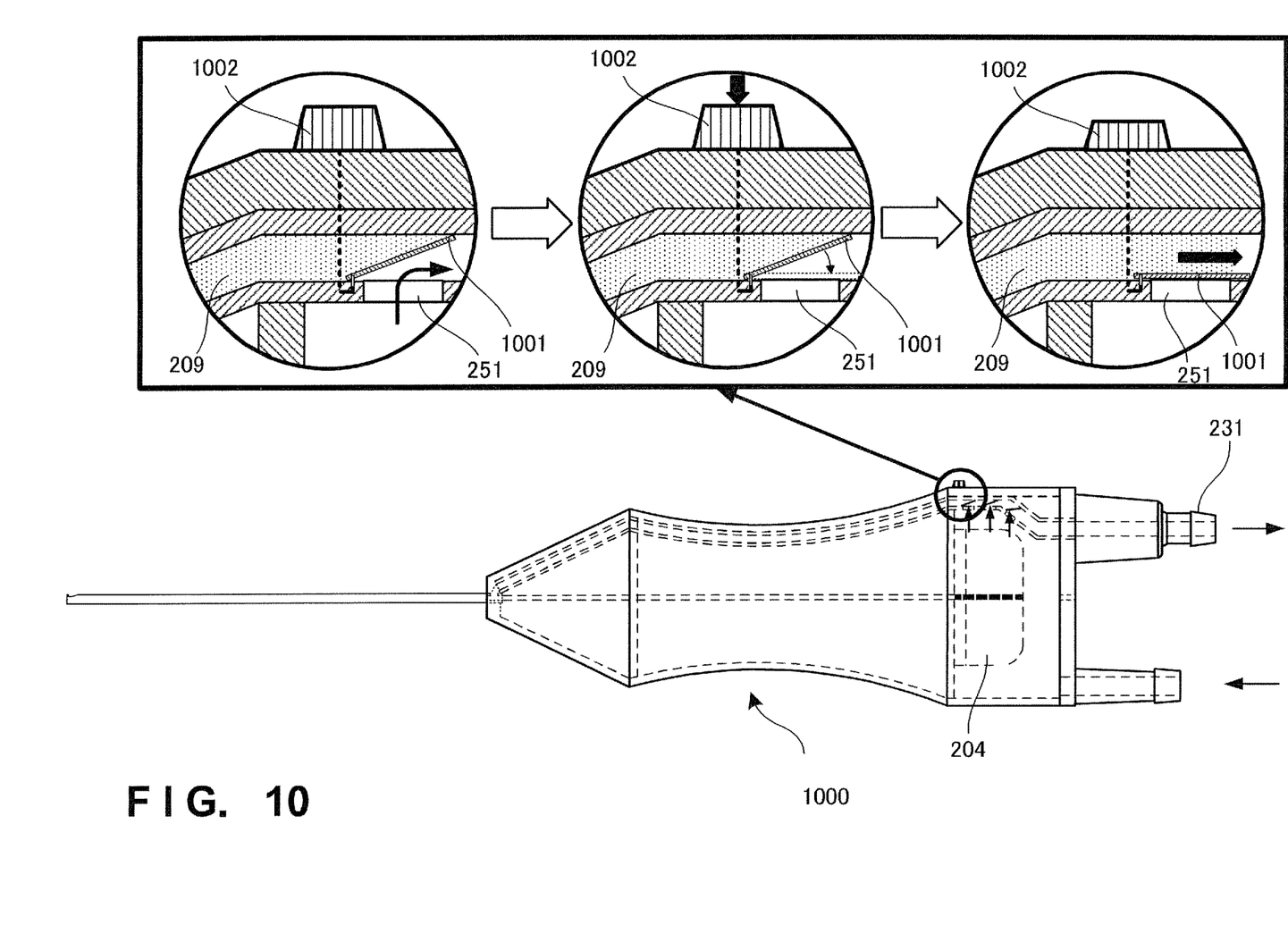
FIG. 10 is a schematic explanatory view of an object suction device according to the third example embodiment of the present invention.

FIG. 10 is a schematic explanatory view of the object suction device 1000 according to the third example embodiment of the present invention. In the channel 209, the valve 1001 that distributes a suction force from a nozzle 231 to one of suction of an object and an air motor is provided. The object suction device 1000 further includes an operation portion 1002 used to perform an opening/closing operation of the valve 1001.

According to the above-described arrangement, it is possible to separate a phase to crush and/or convey an object by rotating the rotating member and a phase to suck the object by the suction force of a negative pressure by a user operation.

Fourth Example Embodiment

An object suction device according to the fourth example embodiment of the present invention will be described with reference to FIG. 11. An object suction device 1100 according to this example embodiment is different from the third example embodiment in that a valve 1101 is pushed down by the pressure of an object in a channel 209 and set an opening portion 251 in a closed state. The rest of the components and operations is the same as in the third example embodiment. Hence, the same reference numerals denote the same components and operations, and a detailed description thereof will be omitted.

Figure 11:
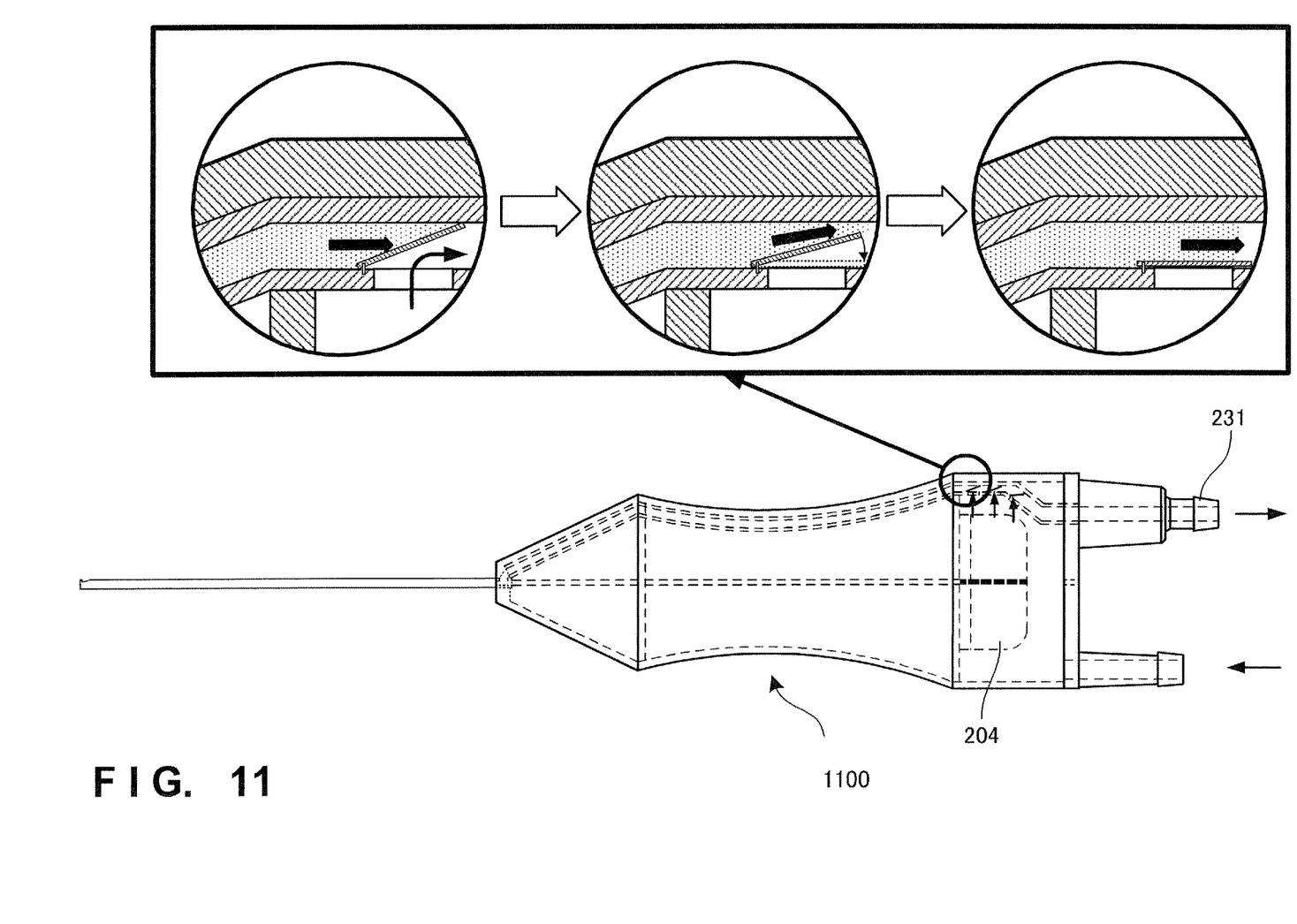
FIG. 11 is a schematic explanatory view of an object suction device according to the fourth example embodiment of the present invention.

FIG. 11 is a schematic explanatory view of the object suction device 1100 according to the third example embodiment of the present invention. In the channel 209, the valve 1101 that distributes a suction force from a nozzle 231 to one of suction of an object and an air motor is provided. Normally, the valve 1101 is maintained at a position to open the opening portion 251 by the biasing force of a biasing means (not shown; for example, a spring). However, when an object flows in the channel 209 and hits the valve 1101, the valve 1101 is moved by the pressure, and the opening portion 251 is set in the closed state.

According to the above-described arrangement, it is possible to crush and/or convey an object by rotating the rotating member in the initial state and, when the object is conveyed in the channel, intensively apply the suction force of a negative pressure to the object in the channel.

Other Example Embodiments

While the invention has been particularly shown and described with reference to example embodiments thereof, the invention is not limited to these example embodiments. It will be understood by those of ordinary skill in the art that various changes in form and details may be made therein without departing from the spirit and scope of the present invention as defined by the claims.

The invention claimed is:

1. An object suction device comprising:
   a pipe;
   a rotating member that is rotatably provided in the pipe and is configured to convey an object that enters from an opening portion provided at a distal end of the pipe toward a rear end of the pipe;
   an air motor that rotates the rotating member;
   a nozzle to suck the object discharged from the rear end of the pipe;
   a channel that is connected to both the nozzle and the air motor, the channel forming a flow of air to pass the object; and
   a valve provided in the channel that is operable, in a first position, to distribute a suction force from the nozzle to suction of the object and, in a second position, to distribute the suction force from the nozzle to the air motor,
   wherein the valve is configured to be operated by the object sucked in the channel to close an opening that makes the channel and the air motor communicate with each other.

2. The object suction device according to claim 1, further comprising an operation portion that performs an operation of the valve to move the valve between the position and the second position.

3. The object suction device according to claim 1, further comprising a biasing unit that applies a biasing force to the valve.

* * * * *